US011224703B2

(12) United States Patent
Kadel et al.

(10) Patent No.: US 11,224,703 B2
(45) Date of Patent: Jan. 18, 2022

(54) MICROSTRUCTURED NOZZLE AND PRODUCTION THEREOF

(71) Applicant: Boehringer Ingelheim MicroParts GmbH, Dortmund (DE)

(72) Inventors: Klaus Kadel, Witten (DE); Lothar Keydel, Dortmund (DE)

(73) Assignee: BOEHRINGER INGELHEIM MICROPARTS GMBH, Dortmund (DE)

( * ) Notice: Subject to any disclaimer, the term of this patent is extended or adjusted under 35 U.S.C. 154(b) by 645 days.

(21) Appl. No.: 16/075,025

(22) PCT Filed: Feb. 2, 2017

(86) PCT No.: PCT/EP2017/052189
§ 371 (c)(1),
(2) Date: Aug. 2, 2018

(87) PCT Pub. No.: WO2017/134127
PCT Pub. Date: Aug. 10, 2017

(65) Prior Publication Data

US 2019/0038850 A1 Feb. 7, 2019

(30) Foreign Application Priority Data

Feb. 4, 2016 (EP) .................................... 16154191

(51) Int. Cl.
*A61M 11/00* (2006.01)
*B05B 1/14* (2006.01)
(Continued)

(52) U.S. Cl.
CPC ......... *A61M 11/003* (2014.02); *A61M 11/007* (2014.02); *A61M 15/009* (2013.01);
(Continued)

(58) Field of Classification Search
CPC .............. B29C 45/372; B29C 45/2673; B29C 45/2675; B29C 2045/2638; B29C 33/306; B29C 33/32; B29C 2033/426
See application file for complete search history.

(56) References Cited

U.S. PATENT DOCUMENTS 6,764,924 B2 7/2004 Gmur
6,846,413 B1 1/2005 Kadel et al.
(Continued)

FOREIGN PATENT DOCUMENTS

DE 4236037 A1 4/1994
DE 4240857 A1 6/1994
(Continued)

OTHER PUBLICATIONS

Bissacco "Precision manufacturing methods of inserts for injection molding of microfluidic systems", Technical University of Denmark (Year: 2005).*

(Continued)

*Primary Examiner* — Jacob T Minskey
*Assistant Examiner* — Virak Nguon
(74) *Attorney, Agent, or Firm* — Matthew B. Dernier, Esq.

(57) ABSTRACT

The invention relates to a nozzle for use in a device for administering a liquid medical formulation, to a method for producing the nozzle in the form of a microfluidic component and to a tool for producing microstructures of the microfluidic component. The nozzle is formed by a plastics plate with groove-like microstructures which are covered by a plastics cover on the longitudinal side in a fixed manner. The production method includes a moulding process in which a moulding tool is used, which moulding tool has complementary metal microstructures which have been pro-
(Continued)

duced from a semiconductor material in an electrodeposition process by means of a master component.

18 Claims, 9 Drawing Sheets

(51) Int. Cl.

| | |
|---|---|
| ***B29C 45/37*** | (2006.01) |
| ***B81C 99/00*** | (2010.01) |
| ***B29C 33/42*** | (2006.01) |
| ***A61M 15/02*** | (2006.01) |
| ***A61M 15/00*** | (2006.01) |
| ***B29C 45/26*** | (2006.01) |
| ***B29L 31/00*** | (2006.01) |
| ***B29C 45/00*** | (2006.01) |
| ***B29C 33/32*** | (2006.01) |
| ***B29C 33/30*** | (2006.01) |
| ***B29K 705/08*** | (2006.01) |

(52) U.S. Cl.

CPC ............. *A61M 15/025* (2014.02); *B05B 1/14* (2013.01); *B29C 33/424* (2013.01); *B29C 45/2673* (2013.01); *B29C 45/372* (2013.01); *B81C 99/009* (2013.01); *B81C 99/0085* (2013.01); *A61M 2205/0244* (2013.01); *A61M 2205/0272* (2013.01); *A61M 2207/10* (2013.01); *B29C 33/306* (2013.01); *B29C 33/32* (2013.01); *B29C 45/2675* (2013.01); *B29C 2033/426* (2013.01); *B29C 2045/0094* (2013.01); *B29C 2045/2638* (2013.01); *B29K 2705/08* (2013.01); *B29L 2031/753* (2013.01); *B29L 2031/756* (2013.01); *B81B 2201/058* (2013.01)

(56) References Cited

U.S. PATENT DOCUMENTS

| | | | | |
|---|---|---|---|---|
| 6,988,496 | B1 | 1/2006 | Eicher | |
| 9,283,333 | B2 | 3/2016 | Hausmann | |
| 2004/0104507 | A1 | 6/2004 | Gmur | |
| 2004/0159319 | A1 | 8/2004 | Kadel et al. | |
| 2006/0016449 | A1 | 1/2006 | Eicher | |
| 2006/0032494 | A1 | 2/2006 | Kadel et al. | |
| 2008/0106001 | A1* | 5/2008 | Slafer | B29C 33/3857 264/310 |
| 2013/0199521 | A1 | 8/2013 | Hausmann | |
| 2013/0292879 | A1 | 11/2013 | Disawal et al. | |
| 2015/0061189 | A1 | 3/2015 | Reiter | |

FOREIGN PATENT DOCUMENTS

| | | | | |
|---|---|---|---|---|
| DE | 19742439 | C1 | 10/1998 | |
| EP | 0537953 | A2 | 4/1993 | |
| EP | 1422193 | A1 | 5/2004 | |
| JP | 1975103699 | A | 8/1975 | |
| JP | 1984039908 | U | 3/1984 | |
| JP | 2001334532 | A | 5/2000 | |
| JP | 2001334532 | A * | 12/2001 | |
| JP | 2012089792 | A * | 5/2012 | |
| WO | WO-9214596 | A1 * | 9/1992 | B23Q 3/1546 |
| WO | 9407607 | A1 | 4/1994 | |
| WO | 9712687 | A1 | 4/1997 | |
| WO | 9916530 | A1 | 4/1999 | |
| WO | 1999016530 | A1 | 4/1999 | |
| WO | 9943571 | A1 | 9/1999 | |
| WO | 0049988 | A2 | 8/2000 | |
| WO | 2001076849 | A1 | 10/2001 | |
| WO | 2005000476 | A1 | 1/2005 | |
| WO | 06136426 | A1 | 12/2006 | |
| WO | 07051536 | A1 | 5/2007 | |
| WO | 2007101557 | A2 | 9/2007 | |
| WO | 2007128381 | A1 | 11/2007 | |
| WO | 2008138936 | A2 | 11/2008 | |
| WO | 09047173 | A1 | 4/2009 | |
| WO | 2009103510 | A1 | 8/2009 | |
| WO | 2009115200 | A1 | 9/2009 | |
| WO | 2012007315 | A1 | 1/2012 | |
| WO | 2013165415 | A1 | 11/2013 | |

OTHER PUBLICATIONS

Bassacco et al., "Precision manufacturing methods of inserts for injection molding of microfluidic systems", Technical University of Denmark, 2005, 7 pages.

Elders et al., "Deemo: A new technology for the fabrication microstructures", Proceeding of the workshop on microelectrical mechanical systems, 1995, pp. 238-243.

International Search Report and Written Opinion for corresponding application, PCT/EP2017/052189, dated Mar. 21, 2017.

Shen,et al., "Fabrication of Integrated Nozzle Plates for inkjet print head using microinjection process," Sensors and Actuators A 127: Physical, Elsevier B. V., pp. 241-247, Dec. 2, 2005.

* cited by examiner

MICROSTRUCTURED NOZZLE AND PRODUCTION THEREOF

The present invention relates to microstructured nozzles and to the production thereof, wherein the microstructured nozzles are suitable in particular for use in devices such as preferably atomisers for administering liquid medical formulations.

An atomiser, by which liquid drug formulations for inhalation are atomised from a container containing a plurality of units of the formulation by means of a microstructured nozzle, is disclosed in WO97/12687A1 and WO09/047173A2. This purely mechanical, miniaturised high-pressure atomiser forms the starting point for the technical development set out here. With this atomiser, a liquid drug formulation from a rigid container with inner bag inserted in the atomiser, as disclosed in WO00/49988A2, is conveyed out of the inner bag by means of a piston pump driven by a worm gear and is atomised by means of a spring-operated pressure generator in a predetermined quantity through a microstructured nozzle to produce a respirable aerosol. Details of possible microstructures for a discharge nozzle employed in the atomisers are disclosed in the documents WO94/07607A1, WO99/16530A1, WO05/000476A1 and WO2007/101557A2.

A method for producing the nozzle bodies is disclosed in the document DE4236037A1. Accordingly, the nozzle bodies are composed of two plates, a base plate with groove-like structures, wherein the grooves connect an inlet region on one side of the plate to nozzle structures formed on the opposite side. In this case, the base plate is made of silicon and is covered by an unstructured plate made of glass. The hollow spaces in the nozzle body in this case usually have rectangular cross sections. The groove structures for a plurality of nozzles are produced simultaneously on a relatively large surface in a parallel manufacturing process which includes a photo-optical lithography process in conjunction with ion-assisted reactive dry etching, and in one step are joined to the cover plate by anodic bonding. Then, using a high-speed diamond circular saw, this composite is divided into individual cuboids and inlet and outlet openings in the nozzle body are exposed. In this splitting process, due to the materials to be split, breakages potentially occur on the side walls and edges of the nozzle bodies, and these breakages should be avoided during operation of the saw since they can lead to unwanted cross-sectional changes to the outlet geometry. Furthermore, the size of the batch produced in the described process is governed inter alia by the size of the silicon plate used and thus, based on the mass production, is limited to the size of conventionally obtainable silicon wafers.

The object of the present invention is to provide a method for producing nozzles, in particular for installation in an atomiser, which method is improved relative to the prior art in particular with regard to mass production. In particular, in this case nozzles in the form of microfluidic components are considered. In particular, a method is to be specified, by which in serial operation large numbers of items can be produced in a short time or large quantities of components per batch can be produced.

Furthermore, a nozzle which is improved in particular with regard to its suitability for mass production, and an improved device containing this nozzle for administering liquid medical formulations, are to be specified.

This object is achieved according to the invention by a nozzle in accordance with claim 1 and by a device in accordance with claim 8.

Furthermore, the object is achieved according to the invention by a method for producing a nozzle in accordance with claim 18.

A feature of the present invention is that the nozzle is made of plastics material or is a microfluidic component made of plastics material and the microstructures of the nozzle are produced at least in part in a moulding process. Such a choice of material generally produces a cost-effective starting material in the manufacture of components or the manufacture of nozzles and gives rise to the possibility of fast production processes. Particularly preferably, the nozzle is made of a rigid plastics material or rigid plastics materials. Possible plastics materials for such manufacture are COC, COP, polycarbonates, polystyrene, polypropylene, PEEK, PMP, PA, PBT or PMMA, for example.

A further feature of the present invention is that the method for producing the nozzle or the microfluidic component includes a moulding process in which a moulding tool is used, which has a microstructure preferably of metal complementary to the microstructures in the microfluidic component to be produced (i.e. the complementary microstructure constitutes a negative of the microstructures to be produced). The complementary microstructure of the moulding tool is, as described later, particularly preferably produced from a semiconductor material in an electrodeposition process by means of a master component.

The moulding tool preferably contains a punch (in particular if the moulding process is a hot stamping process or compression injection moulding process) or a negative mould or a mould insert (in particular if the moulding process is an injection moulding process), wherein a surface of this punch or of this negative mould or of this mould insert exhibits the complementary microstructure. Since the tool should be used as often as possible for moulding before it becomes unusable due to wear, the shaping surfaces of the tool are preferably made of a robust material, in particular of metal, silicon or hard ceramic. A method for producing a tool provided with microstructures for stamping a plastics layer or for overmoulding with casting resin is known from DE4240857A1. In this case, a LIGA process (lithography, electroplating and moulding) is described, in which the tool is produced by electroplating of a die which has on one side the same microstructure bodies which are to be produced on the plastics layers by the tool. The die itself is produced by coating of a metallic base plate (chromium nickel steel) with a layer of PMMA (polymethyl methacrylate), which is structured by means of X-ray lithography or, if another non-conductive layer is used, by means of other in particular mechanical processes, in such a way that the metal is exposed in the interstices of the structure. This metallic structure base is then used as a cathode in the electroplating. The dies in such a method are not recyclable if X-ray lithography is used and are only reproducible to a very limited degree in the event of mechanically structuring in the production of small structures.

EP1422193A1 discloses a method for producing a tool insert for injection moulding of a microstructured part which has an arrangement of microstructures on an outer surface of the part. The method comprises a multiplicity of steps: the application of an etched marking to a first wafer, the formation of an arrangement of microstructures by means of plasma etching on the front face of the first wafer (wherein the wafer is etched through at the corresponding locations), the bonding of the first wafer to a supporting substrate for formation of a master, the electrochemical deposition of a metal layer on the rear face of the first wafer and at the etched-through locations and the separation of the metal layer from the master, wherein the metal layer can be used as a shaping part of a tool insert.

At this point, a subsidiary object to the above-mentioned object was revealed, namely that for use in a moulding process an improved moulding tool with complementary microstructures is to be provided. In particular, the production of a complementary microstructure for use in a punch or a negative mould or mould insert or for a tool insert (e.g. for injection moulding processes) is to be specified. In particular, the production of the complementary microstructure or the microstructured tool inserts themselves (with regard to replacement in the event of wear) is also very reproducible.

This subsidiary object is achieved according to the invention by a moulding tool in accordance with claim 9.

Advantageous developments are described below and in detail with reference to the drawings.

At this point, for production of a microstructure on a moulding tool a method is used which includes the use of a microstructured master component made of a semiconductor material, in particular of highly doped silicon. Due to the given usability of methods available from semiconductor technology, microstructures can be produced in master components with high precision and good reproducibility. In this case, the use of highly doped semiconductors, in particular highly doped silicon, as material for the master component is particularly preferred. It has been shown that by using such semiconductors with a good conductivity the corresponding master components can be used as non-conductive master components in significantly streamlined moulding processes (in this case for producing a moulding tool). By comparison with the use of non-conductive master components various steps in the moulding process for producing a shaping tool can be omitted, so that the resulting process can be quicker and more cost-effective and, because it is less complex, potentially also less prone to faults. In particular, in the case of moulding of the master component based on electroplating the conductive master component itself can be used directly as a cathode without previously obtaining a metal plating. Thus process steps which relate to the metal plating can be omitted. As an alternative to the use of master components made of semiconductor materials, master components made of metal can also be used which have been structured by means of microsystem technologies, such as laser drilling or micromilling in particular. However, the microstructures in the master component are preferably produced in particular for the described application by means of structuring processes from semiconductor manufacture. By comparison with methods such as laser drilling and micromilling, a lithographic structuring in semiconductor materials offers the possibility of producing finer structures with, if required, higher reproducibility.

Particularly preferably, the master component is produced in a photolithographic process in conjunction with an ion-assisted reactive dry etching process preferably of silicon.

A further feature of the invention is that the master component has a multiplicity of microstructure groups, wherein a "microstructure group" here corresponds to the microstructures of each microfluidic component to be produced (i.e. the master component has the microstructures of a plurality of microfluidic components to be produced, i.e. of a plurality of nozzles to be produced). The microstructure groups are preferably arranged in parallel rows and columns on the master component or on a surface of the master component which is flat except for the microstructures. By the arrangement of a multiplicity of microstructure groups on the master component it is possible to produce a moulding tool (or a part of a moulding tool or a tool insert) with a similar multiplicity of complementary microstructure groups, so that when this moulding tool is used in a moulding process this multiplicity of microstructure groups can be produced serially in one production batch.

The production of such a master component with a multiplicity of parallel microstructure groups is possible by the application of the mentioned structuring processes from semiconductor production. These structuring processes exhibit a high precision with structural accuracies of several micrometres down to the submicrometre range. Furthermore, the methods used here for the production of the master component are themselves suitable for series production so that the master components themselves and thus also the moulding tools can be produced again by the method used rapidly and with a high reproducibility. Thus, for example in mass production of microstructures by plastics injection moulding, a worn moulding tool can be quickly replaced, without relatively long machine shutdown times, by a new tool which meets the requirements, or the tools can be easily stored for such a replacement. Likewise, identical tools can be produced by series production for simultaneously proceeding moulding processes.

A preferred method for producing a moulding tool with complementary microstructures (or the part of a moulding tool or a tool insert which has complementary microstructures) generally has, for example, the following, in particular consecutive steps (here in some instances steps are also carried out which can be omitted in the preferred use of semiconductor materials for the master component, in particular for the use of highly doped semiconductor materials):

- producing a master component with microstructures;
- (optionally) metallising the surface of the master component or applying a metallisation layer to the surface of the master component, which has the microstructures, wherein gold is preferably used for metallisation, wherein particularly preferably an adhesive layer preferably made of chromium is applied before the metallisation;
- electroplating of a metal (preferably nickel or containing nickel) on the preferably metallised surface of the master component (in this case a layer thickness of at least 500 μm metal is preferably deposited);
- (preferably) boundary-edge processing on the workpiece, on which the metal has been electroplated, for example by producing an outer contour through die-sinking in the electroplated metal layer, optionally with subsequent sawing of the workpiece in the gap produced by die-sinking;
- separating the deposited metal layer (which as a metal plate or metal foil is part of the later moulding tool), optionally including the layer of the master component produced during metallisation, in particular by wet-chemically dissolving the master component;
- (optionally) where appropriate, removing an adhesive layer (for example chromium) which has been deposited in a preceding metallisation, in particular by etching (for example in particular selectively with Cer(IV)-ammonium nitrate);
- (optionally) boundary-edge processing of the metal plate or metal foil, wherein first of all a structure protection is applied to the complementary microstructures in the deposited metal layer, then the boundary edges (i.e. outer shaping of the part of the moulding tool produced here or the tool insert produced here for a moulding tool) are processed and the structure protection is removed again.

With this method, a metal plate or metal foil is produced which has the complementary microstructures and can now be used as part of a moulding tool or tool insert, for example in that it is applied to a punch for hot stamping processes or is part of the inner wall of a hollow mould in an injection moulding process.

A further feature of the moulding tool according to the invention is that optionally in the moulding tool a plurality of metal plates or metal foils with complementary microstructures are used (this is possible due to the high reproducibility in the above-mentioned production process for the metal plates or metal foils). In this way, the number of microstructure groups which are moulded in an application of the moulding process (for example, hot stamping process or above all an injection moulding process) (and from which the individual microfluidic components or nozzles are produced) can be multiplied without the size of the regions with complementary microstructures in the moulding tool overall being limited, for example by the size of the equipment used in the preceding method steps. In this way (both by the use of master components with a multiplicity of microstructure groups and also by the arrangement of a plurality of metal plates or metal foils with complementary microstructures in the moulding tool), it is possible to produce moulding tools for the production of almost any large number of microstructure groups and thus of microfluidic components per production batch.

A further feature of a method according to the invention for producing a microfluidic component, in this case a nozzle, is that the metal plate or metal foil which has the complementary microstructures and is used as part of a moulding tool or as a tool insert is retained in the tool at least partially by magnets. Particularly preferably, the moulding tool in which liquid plastics material is injected in the injection moulding process has two parts: a first part, on which the metal plate or metal foil with the complementary microstructures is magnetically retained, and a second part which is preferably dish-shaped or in the form of a half-dish, with which the metal plate or metal foil is firmly clamped at its edges in the tool. In the case of long-term use in punches or injection moulding processes and the like, the complementary microstructures are susceptible to wear; and due to the magnetic retention in the tool, the metal plate or metal foil with the complementary microstructures can be easily replaced (this also applies for an additional retention by clamping). For this purpose, it is expedient that the metal plate or metal foil is made of a ferromagnetic material, such as for example nickel or nickel iron or nickel cobalt.

A plastics injection moulding process is preferably used for the production of the microfluidic component or of a basic body having the microstructures (which constitutes a semi-finished product in the production of the microfluidic component). For this purpose, the use of nickel or in particular nickel cobalt as material for the metal plate or metal foil with the complementary microstructures is likewise particularly suitable, since these materials are still dimensionally stable even at relatively high temperatures such as are used in plastics injection moulding processes.

In the injection moulding process, the retention means of the metal plate or metal foil with the complementary microstructures must withstand the demoulding forces, which are produced for example during opening or starting of the tool or during removal of the moulded basic body having the microstructures. These demoulding forces are usually so great that retention based upon suction or negative pressure or a vacuum is not sufficient. Magnets made of samarium cobalt (SmCo) are preferably used in the method according to the invention, since it has been shown that even at relatively high temperatures (for example in the range around 200°, in which some plastics materials can already be processed in the injection moulding process) they also retain their magnetic capability, but at which other magnets, such as those for example made of NdFeB, already lose their magnetic capabilities.

Particularly preferably, a plurality of individual SmCo magnets are used and are arranged adjacent to one another in the retention of the metal plate or metal foil so that the poles directed towards the metal plate or metal foil (**106*f*) alternate in their polarisation. In this case, flat magnets are preferably used. The magnets (111) are preferably arranged so that in each case a side edge of a magnet (111) borders on the metal plate or metal foil (106*f*) and that the poles of magnets (111**) in each case arranged adjacent to one another alternate or differ with regard to their polarisation (in particular relative to one another).

Surprisingly, it has been shown that the magnetic retaining forces, which act on the ferromagnetic metal plate or metal foil, can be intensified by such an arrangement. In this case, in particular rectangular, plate-shaped SmCo magnets are used, the poles of which in each case lie on the flat sides. The side edges or in particular long edges form, where appropriate together with the long edges of separating plates optionally arranged between the magnets, a bearing surface for the metal plate or metal foil.

A further feature of the present invention is that the microfluidic component or the nozzle (for example for use in a device for administering a liquid medical formulation) is assembled or formed from at least two plastics parts. The two plastics parts are preferably substantially plate-shaped and are assembled or connected to one another so that the microfluidic structures are located between the plates. In particular, the microstructures, preferably including at least one inlet opening and/or outlet opening, are formed in a plane (parallel to the main extent of the plates) in the microfluidic component. In this case, the microstructures are preferably in the form of grooves on a (preferably otherwise planar) plate, which is covered by a cover which (at least on the side facing the plate) is planar. In the case of a rectangular channel, three walls are thus formed by the plate and the fourth wall is formed by the cover (or the cover plate). Thus the preferably groove-like microstructures on the plate are covered on the long side by the cover. The plate and the cover made of plastics material are firmly or inseparably connected to one another. The cover is preferably made at least in part of a rigid plastics material.

In this case, the plate with the microstructures or a base plate having the microstructures is preferably produced by the method according to the invention or moulding process described in this document, or the microstructures are preferably produced by means of a moulding tool according to the invention. The methods described here are also applicable to microfluidic components which are composed of more than two plastics parts. For example, such a component can be made of two microstructured main bodies or microstructured plate bodies, between which a plate body which is planar on both sides, optionally with through-bores, is located.

According to the invention, the connection between the at least two plastics parts or the connection of the plate and the cover (or base plate and cover) takes place by thermocompression bonding (or ultrasonic welding), laser bonding, plasma-activated bonding or particularly preferably by solvent bonding or polymer bonding (bonding with an additional material such as photoresist). The choice of the method depends inter alia upon the materials of the plate and the cover and whether both are made of the same material. The connection of the plastics components by means of an adhesive is in many cases likewise possible, but in this case it must be ensured that no adhesive collects in the microstructures or can be removed therefrom again without in this case impairing the adhesive connection between the plates themselves. Optionally, before the adhesion of the plates with an adhesive, the microstructures are filled with a further, easily removable material.

For the solvent bonding, a solvent (preferably for microfluidic components with a base plate and plate-shaped covers made of the same material) which is suitable for at least partially dissolving the plastics material used is distributed in a planar manner on at least one of the two plastics parts on the connection side. The solvent is preferably applied in a spin-coating process on the planar surface of the plate-shaped cover or on the cover plate. In this case, the solvent is dosed centrally onto the rotating cover plate. By this spin-coating process a uniform, thin film of the solvent forms on the cover plate, by which the surface is uniformly dissolved. Subsequently, the base plate with its microstructured side is pressed onto the side of the cover processed with solvent and the resulting component is heat-treated (for example heated in a furnace). In this case, the dissolved plastics material of the cover acts as an adhesive between the two plastics components. The treatment of the cover prevents the microstructures themselves from being changed by the use of solvents. The resulting connection between the two plastics parts is a planar connection. Depending upon the individual solubilities of the various plastics materials, different solvents are suitable in each case for use in the solvent bonding of different plastics materials. Thus for example the releasing means dichloromethane is in particular suitable for use in solvent bonding of parts made of PMMA or POM or N-methylpyrrolidone during bonding of parts made of PC or toluene during bonding of parts made of COP or COC or xylene during bonding of PP. The laser bonding of plastics components is preferred in those cases in which one plastics component (preferably the cover) is transparent or translucent and the other is absorption-sensitive with regard to the wavelength of the laser used. The two plastics components are for example laid on one another, and the laser beam is directed or focused through the transparent plastics component onto the surface of the component lying below it. This causes for example a melting of the surface (or another activation of the surface). Preferably due to the effect of pressure (compression), the two plastics parts are joined at the melted or activated surface. Alternatively, the at least two plastics components can also be connected to one another by plasma-activated bonding. This method is suitable for example when both plastics components have microstructures which are directed towards one another during assembly of the microfluidic components (i.e. if the cover is also microstructured). During the plasma-activated bonding, one or both plastics components are plasma-treated, compressed and preferably heat-treated (heated). The activation preferably takes place with an atmosphere-based plasma or with a plasma based on oxygen or a mixture of oxygen and noble gas (for example addition of argon or helium).

Optionally during plasma activation, a plasma-chemical processing is carried out, in which the surfaces of the groove-like microstructures are changed in such a way that depending upon the required application they have hydrophilic or hydrophobic characteristics or coatings. This is achieved for example by the introduction of a precursor gas into the plasma. The precursor gas contains for example fragmented plastics materials and stimulates or functionalises the polymer formation or the establishment of connections.

In the production process according to the invention, the base plate or the at least one microstructured plate preferably has a multiplicity of microstructure groups, which are jointly covered by a cover and only then are they divided, for example in conventional sawing processes, into the microfluidic components to be produced (or, in the case of the application example, nozzles). Depending upon the choice of the material for the base plate and the cover, i.e. in the choice of plastics materials which for example due to a low brittleness are not prone to splintering during sawing, it is preferably possible during sawing to avoid additionally protective process steps, such as for example filling up the microstructures with a protective coating and subsequent dissolving/flushing out of this protective coating. Moreover, the plastics material can be chosen to be sufficiently soft, so that it can be cut up for example using water jet cutting techniques and for example the use of comparatively expensive diamond saw blades or energy-intensive laser cutting processes can be omitted.

To simplify the cutting process, the structures of the moulded base plates preferably have (when transparent materials are used for the cover) cutting markings which orient the cuts by which the capped base plates are disassembled into the individual microfluidic components (or nozzles).

The nozzle preferably serves for atomisation of the liquid medical formulation and has at least one nozzle channel or one nozzle orifice and preferably has a filter structure.

A further feature of the present invention is that the nozzle for the atomisation of medical formulations is produced from a plastics material, wherein the choice of the plastics material depends upon the composition of the medical formulation. When aqueous formulations are used, it is preferable to use materials with hydrophobic characteristics or hydrophobic surfaces, so that in the nozzle outlet region (or at locations where the microfluidic system comes into contact with air) no or only reduced formulation residues collect, which (depending upon the constituents) could otherwise, for example in the event of drying out, form agglomerates which can impair the quality of sprays produced with the nozzles. In this context, it is preferable to use a plastics material with a non-stick effect based on the respective substances of the medical formulation used.

Otherwise, the material of the nozzle is selected so that it is resistant to the solvent contained in the formulation and also is chemically inert relative to the other constituents of the formulation. The main reason for this is naturally that in medical applications the formulation coming out of the nozzle should in no way be altered by the material of the nozzle. Moreover, however, the chemical inertness of the nozzle material has the effect that the potential formation of deposits is reduced. Generally, the production of deposits is a function of the composition of the formulation, the solubility of the constituents thereof, the potential for interaction of the constituents with one another and with device components (such as here with the channel walls in the nozzle) in fluid contact, and the behaviour of the formulation under different climatic conditions, in particular at different temperatures.

The nozzles are preferably produced for example from COC (cyclo olefin copolymer), COP (cyclo olefin polymer), polystyrene, polypropylene, PEEK, PMP (polymethylpentene) or PMMA. In general, it is possible also to produce microfluidic components for example from polycarbonate (PC) (high strength, transparent and colourless), but from the chemical point of view such components can be problematic because of the many oxygen moieties in the material and the resulting reactivity for operation with medical formulations. The same applies to microfluidic components made of PA (polyamide) or PBT (polybutylene terephthalate) because of their susceptibility to chemical cleavage (PA) or their sensitivity relative to hydrolysis (PBT).

In the devices described here for administering liquid medical formulations, atomisers are preferably considered by which liquids are expelled, i.e. atomised or nebulised, via nozzle structures.

In addition to pure liquids and solutions, the term "liquid" additionally covers dispersions, suspensions, solutions (mixtures of solutions and suspensions) or the like. The term "medical formulation" or "drug formulation" is understood in the context of the present invention to include not only medicaments but also therapeutic agents or the like, and thus in particular any type of agents for inhalation or other application.

The term "aerosol" is understood in particular to mean a cloud-like accumulation of a multiplicity of droplets of an atomised liquid, wherein the droplets preferably move at low speeds. In particular in the case of the atomiser considered here, the droplet cloud has a conical shape and a main propagation direction which particularly preferably corresponds to the main flow direction of the liquid in the microfluidic component.

The individual features of the present invention can be used independently of one another or combined with one another.

Further advantages, features, characteristics and aspects of the present invention emerge from the claims and the following description of preferred embodiments with reference to the drawings. In the drawings:

Figure 4A:
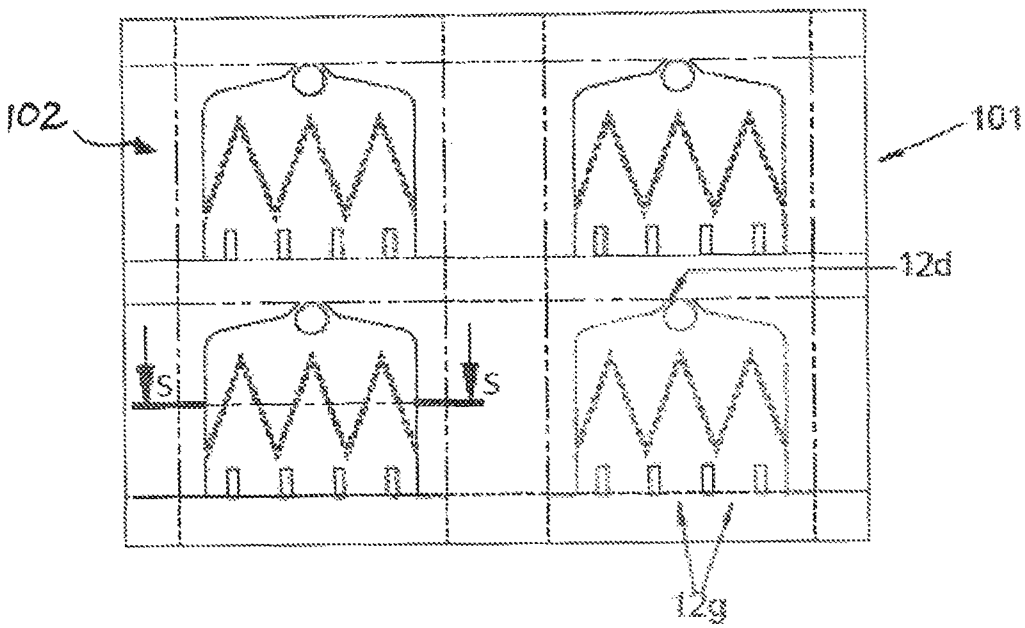
Figure 4B:
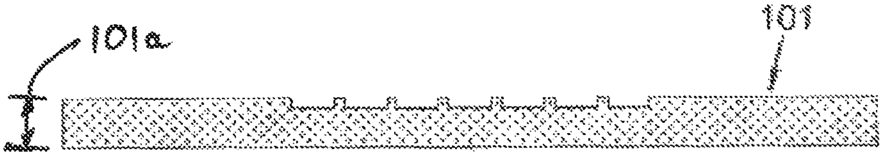
Figure 4C:
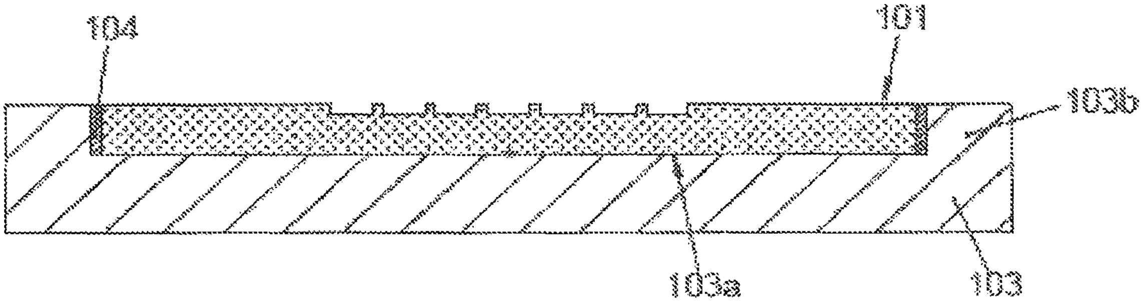
Figure 4D:
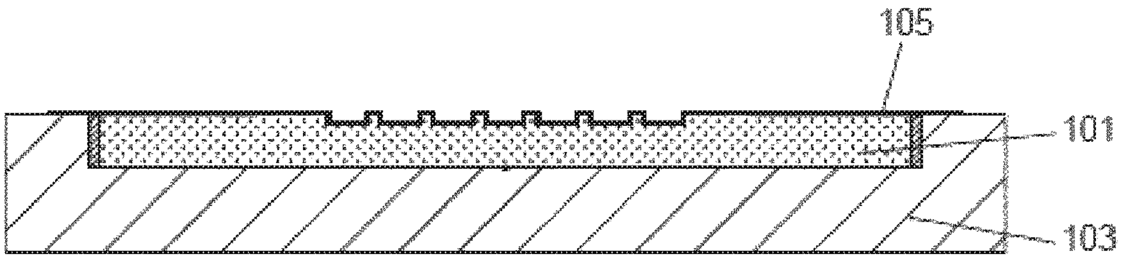
Figure 4E:
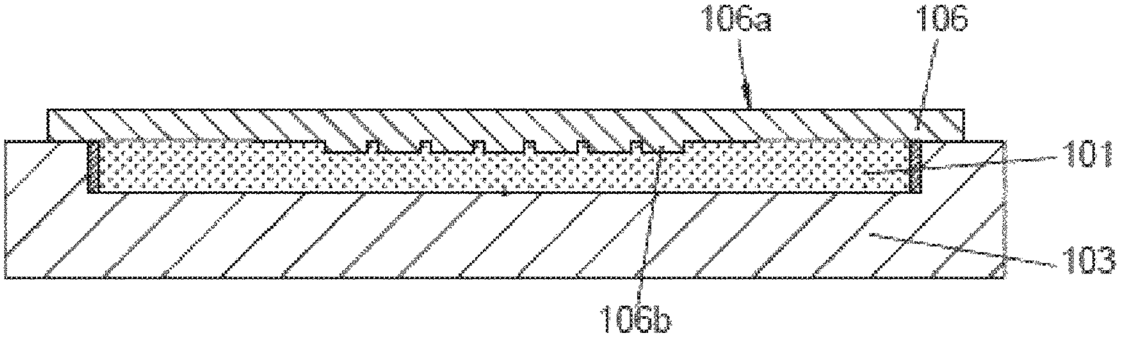
Figure 4F:
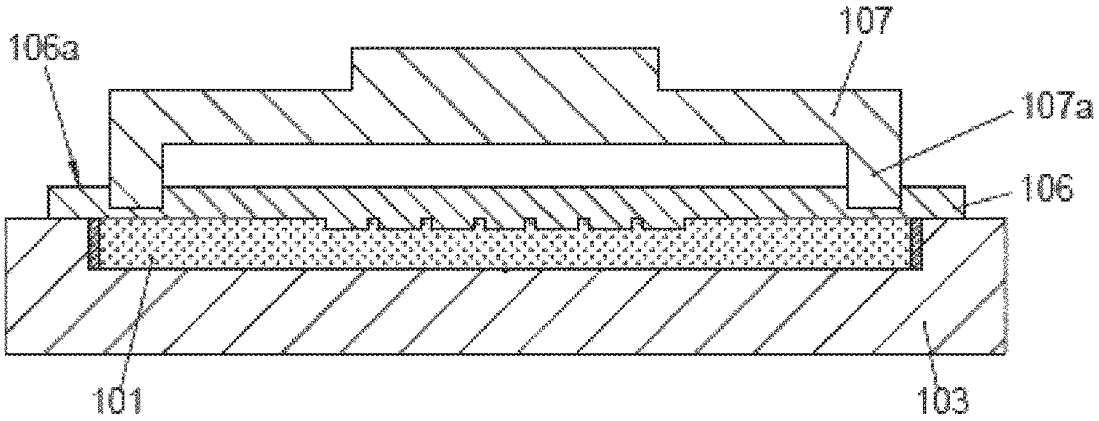
Figure 4G:
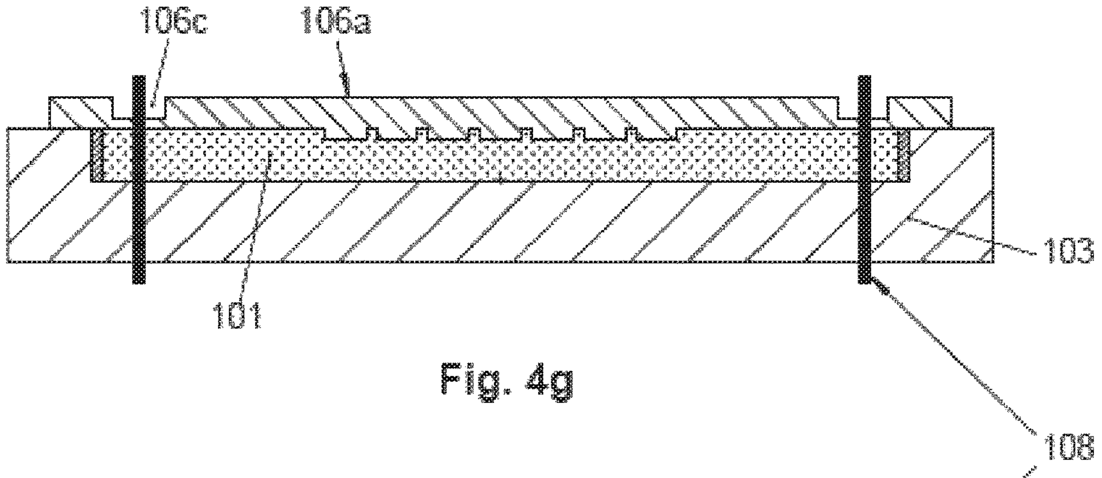
Figure 4H:
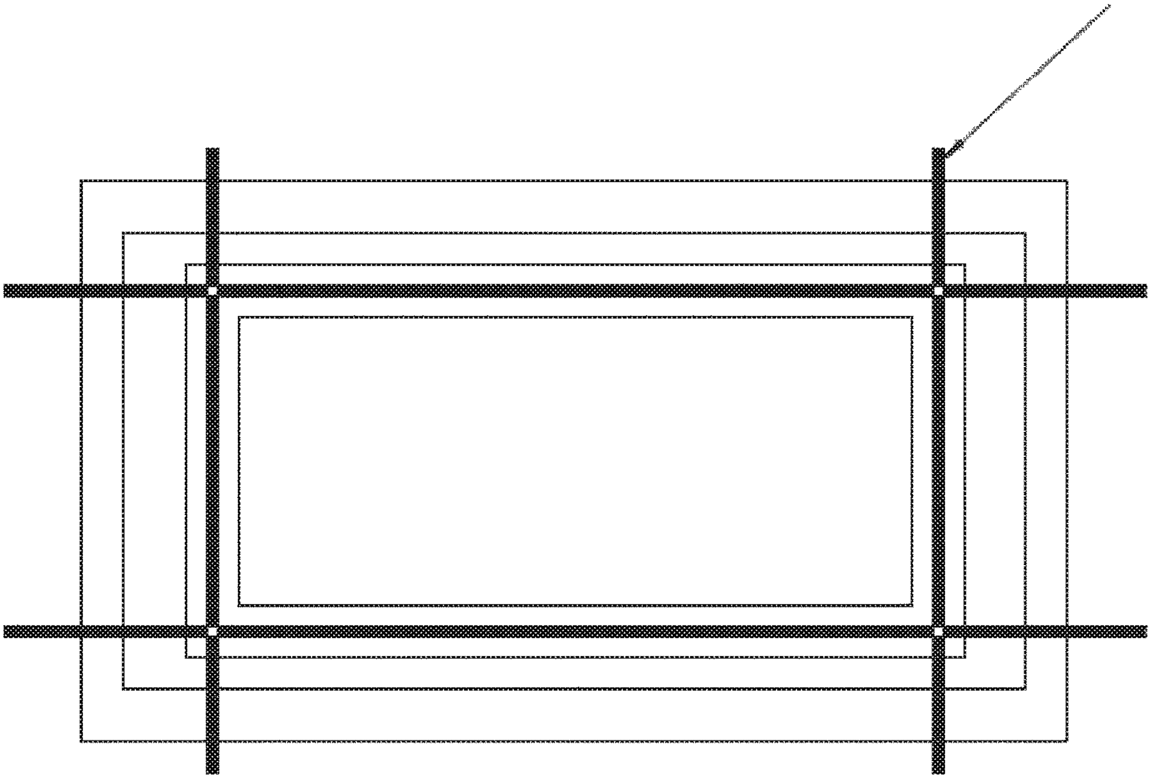
Figure 4I:
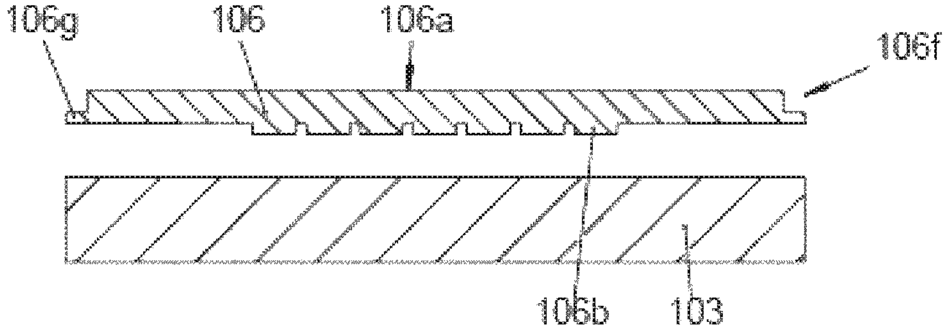
Figure 4J:
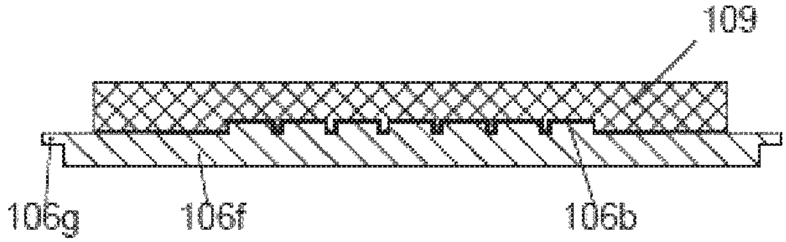
Figure 4K:
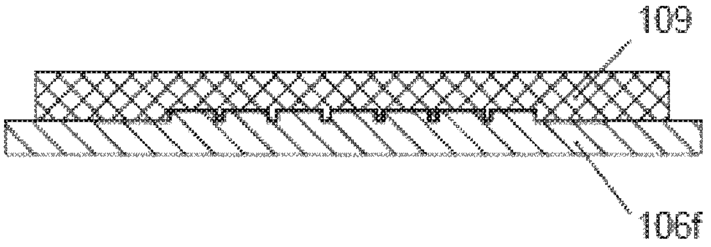
Figure 4L:
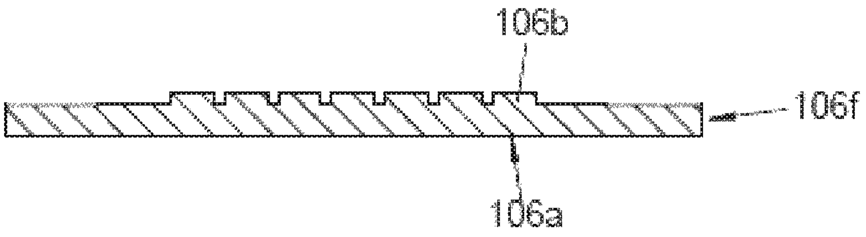
Figure 4M:
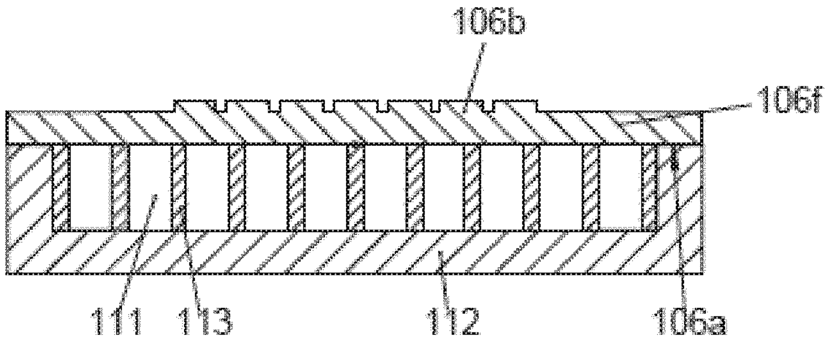
Figure 4N:
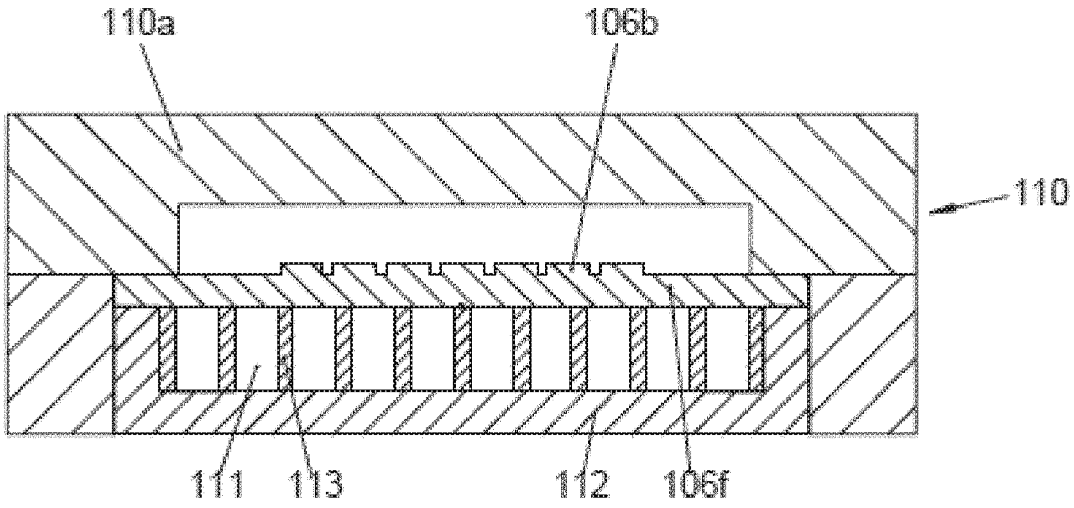
Figure 4O:
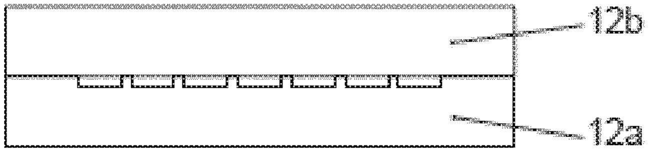
Figure 5A:
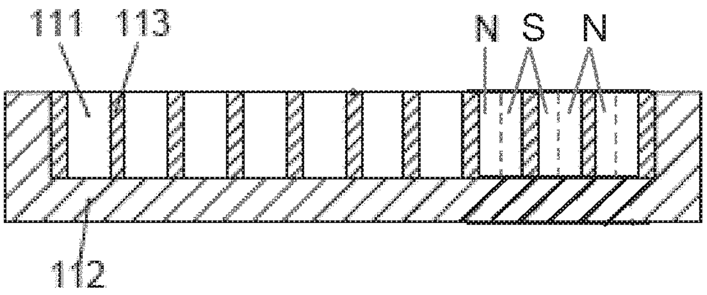
Figure 5B:
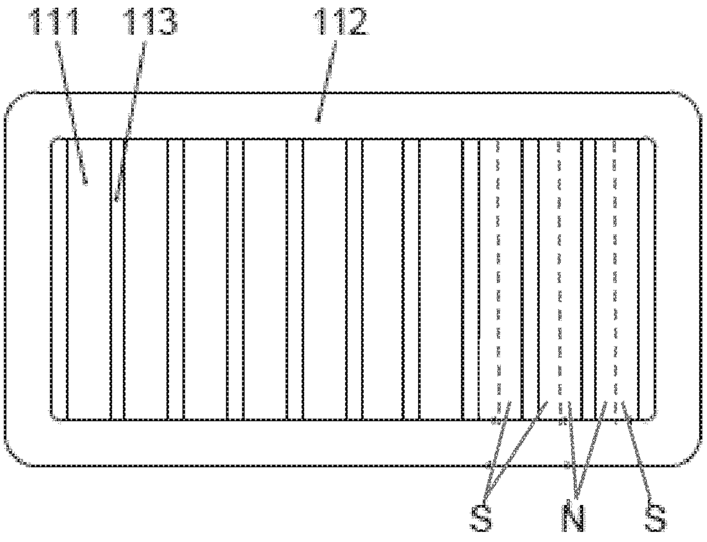

FIG. 4 is a schematic representation of a plurality of sub-steps of a method for producing a moulding tool with microstructures, starting from the plan view of a microstructured master component shown schematically (FIG. 4*a*, with partial sectional view in FIG. 4*b*) via method steps generally shown schematically in cross section (FIGS. 4*c* to 4*m*) for producing the moulding tool and a schematic cross-sectional view of the moulding tool (FIG. 4*n*) to a schematic cross-sectional view of a microfluidic component (or a nozzle) (FIG. 4*o*);

FIG. 5 shows a magnetic retaining plate arrangement for use in a moulding tool.

In the drawings the same references are used for the same or similar components, wherein corresponding or comparable characteristics and advantages are achieved even if a repeated description is omitted.

Figure 1:
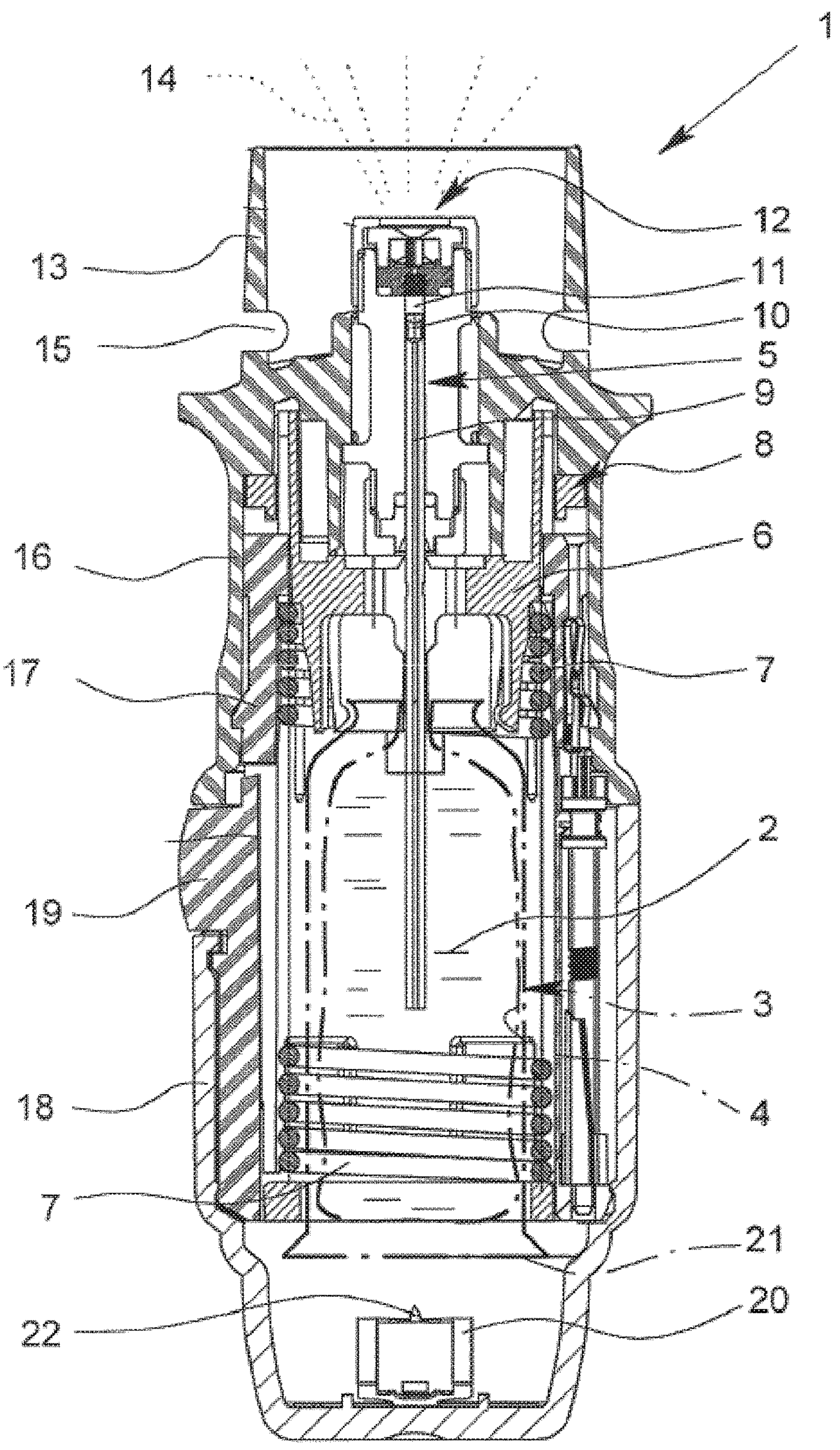
FIG. 1 is a schematic section through an atomiser in the untensioned state.
Figure 2:
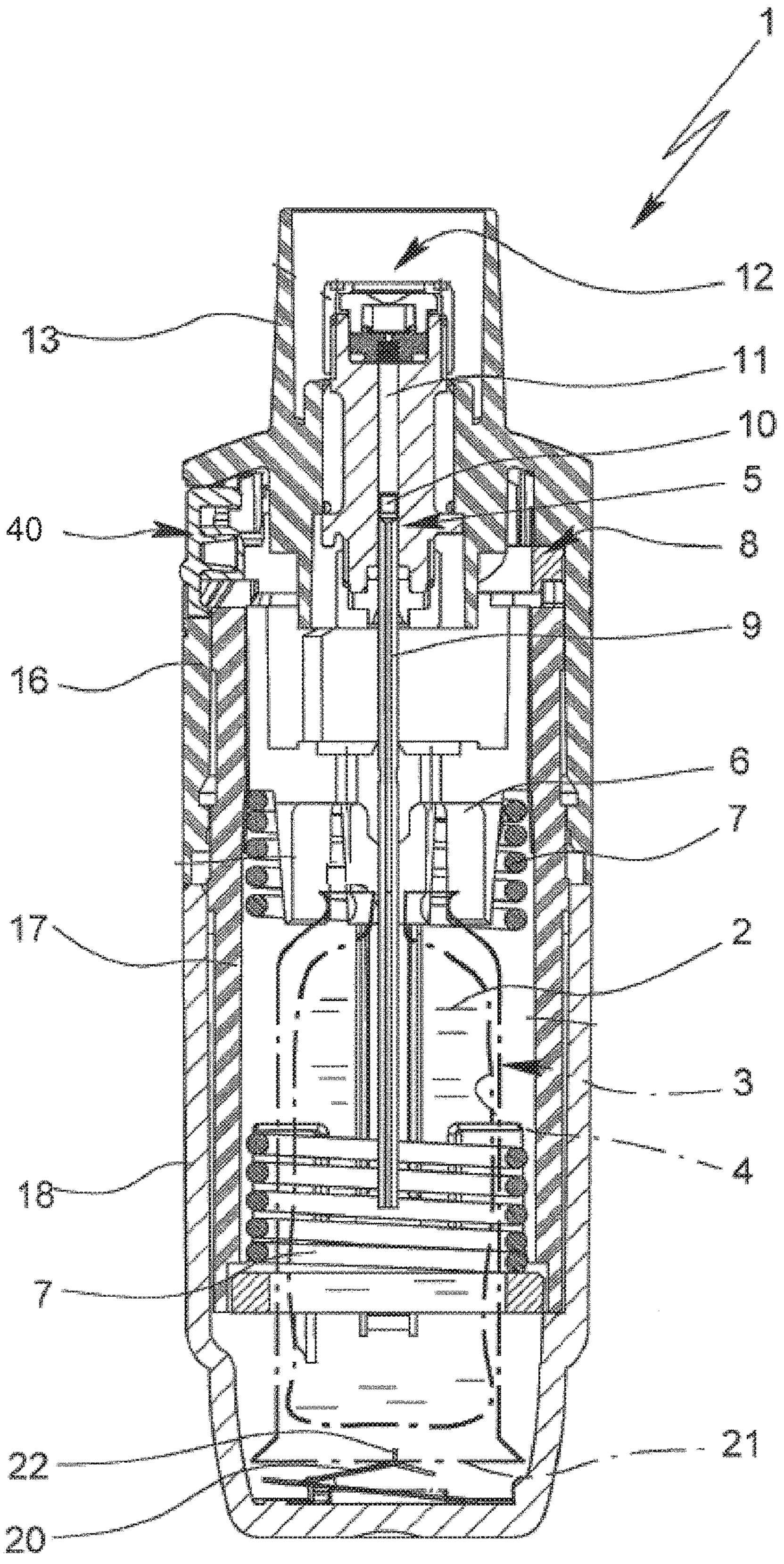
FIG. 2 is a schematic section, rotated by 90° relative to FIG. 1, through the atomiser according to FIG. 1 in the tensioned state.

FIGS. 1 and 2 schematically show a hand-operated medical device in which the proposed nozzle (12) can be used. The device according to FIGS. 1 and 2 is a propellant-free atomiser (1) which, for each actuation cycle, dispenses the respective predetermined quantity of liquid (2) or a liquid medical formulation preferably as a respirable or inhalable aerosol (14) from the nozzle (12). This aerosol (14) comprising droplets with aerodynamic diameters of preferably 0.5 to 10 micrometres, in particular 0.5 to 5 micrometres, can be breathed in with, for example, ambient air flowing in through air intake openings (15) on the mouthpiece (13), by a user (not shown) who puts the atomiser (1) with the mouthpiece (13) to his mouth for this purpose. During operation of the atomiser (1), a distinction is made between the untensioned state with an unfilled metering volume in the pressure chamber (11) (FIG. 1) and the tensioned state with a filled pressure chamber (11) (FIG. 2).

During tensioning of the atomiser (1), the upper housing part (16) thereof is rotated relative to the inner housing part (17) and the lower housing part (18) by a fixed rotation angle of preferably 180°. By means of an internally arranged worm gear, a piston pump is driven by the relative rotation, so that a predetermined, optionally adjustable quantity of liquid (2) is conveyed out of the container (3) into the pressure chamber and simultaneously the drive spring (7) of the pressure generator (5) is tensioned (the end state of the tensioning operation is shown in FIG. 2). When the atomiser (1) is activated, i.e. when a locking ring (8) is actuated by means of a button (40), the energy of the pressure generator (5) stored in the drive spring (7) is released; the hollow piston (9) previously used for conveying liquid now presses with a closed non-return valve (10) into the pressure chamber (11), so that the amount of liquid predetermined by the stroke movement of the hollow piston (9) is expelled from there through the nozzle (12). The device is now again in the untensioned state (FIG. 1).

The hollow piston (9) simultaneously constitutes the connecting element between the pressure chamber (11) and the interior of the container (3). If in the context of the tensioning operation the hollow piston (9) is pulled out partially from the pressure chamber (11), a negative pressure is produced there, by which liquid (2) from the container (3) is introduced into the pressure chamber (11) via the non-return valve (10), open in this situation, in the hollow piston (9). If the hollow piston (9) shoots into the pressure chamber (11) during activation of the atomiser (1), the non-return valve (10) is closed by abutment of its sealing surfaces on the seat in the hollow piston and the liquid in the pressure chamber (11) is expelled under pressure through one or more filters (possible filters and filter systems are described for example in WO2012/007315) and the nozzle (12). The hollow piston (9) and pressure chamber (11) are sealed against one another for example by an elastomeric seal, which in particular is in the form of a O ring and is located in the guide tubes of the piston close to the entry thereof into the pressure chamber (11); the geometric installation situation of this seal, which is preferably compressed by means of a support ring, corresponds for example to the situation described in WO07/051536A1.

In the example shown, the hollow piston (9) is firmly connected—for example injection moulded on, bonded or snapped on—to a holder (6), which belongs to the pressure generator (5), for the container (3). The container (3) is fixed by means of the holder (6), in particular by clamping or latching, in the atomiser (1) so that the hollow piston (9) penetrates into the fluid chamber of the container (3) and/or is fluidically connected to the liquid (2) in the container (3) and it can be drawn in by means of the hollow piston.

The container can be replaceable as required. For this purpose, the equipment housing can be configured so that it can be opened or partially removed (for example in the form of a cap-like lower housing part (18) as disclosed in WO07/128381A1). The container (3), which is used in the atomiser (1) preferably equipped with a dose indicator or a meter, is designed for the removal of a plurality of dosage units. For this, it must be designed so that even in the event of withdrawal of liquid the internal pressure remains substantially unchanged, so that the same amount of liquid (2) is always withdrawn during intake. In this connection, in principle, it is possible to use not only a container (3) with a rigid vessel wall, of which the internal pressure is kept constant by means of ventilation and as described for example in WO06/136426A1, but also a container (3) with a flexible wall which, when liquid is withdrawn, moves at least partially into the interior of the container in such a way that the internal pressure is kept constant by reduction of the internal volume of the internal pressure. In this case, containers (3) are preferred, in which the flexible wall is formed by a bag (4) which is substantially deformable, compressible and/or contractible. Such containers are described in various embodiments in the documents WO00/49988A2, WO01/076849A1, WO99/43571A1, WO09/115200A1 and WO09/103510A1. In the embodiment shown, the atomiser (1) has for example a piercing element (22) which is mounted on a spring (20) and enables ventilation in the container base (21).

Figure 3:
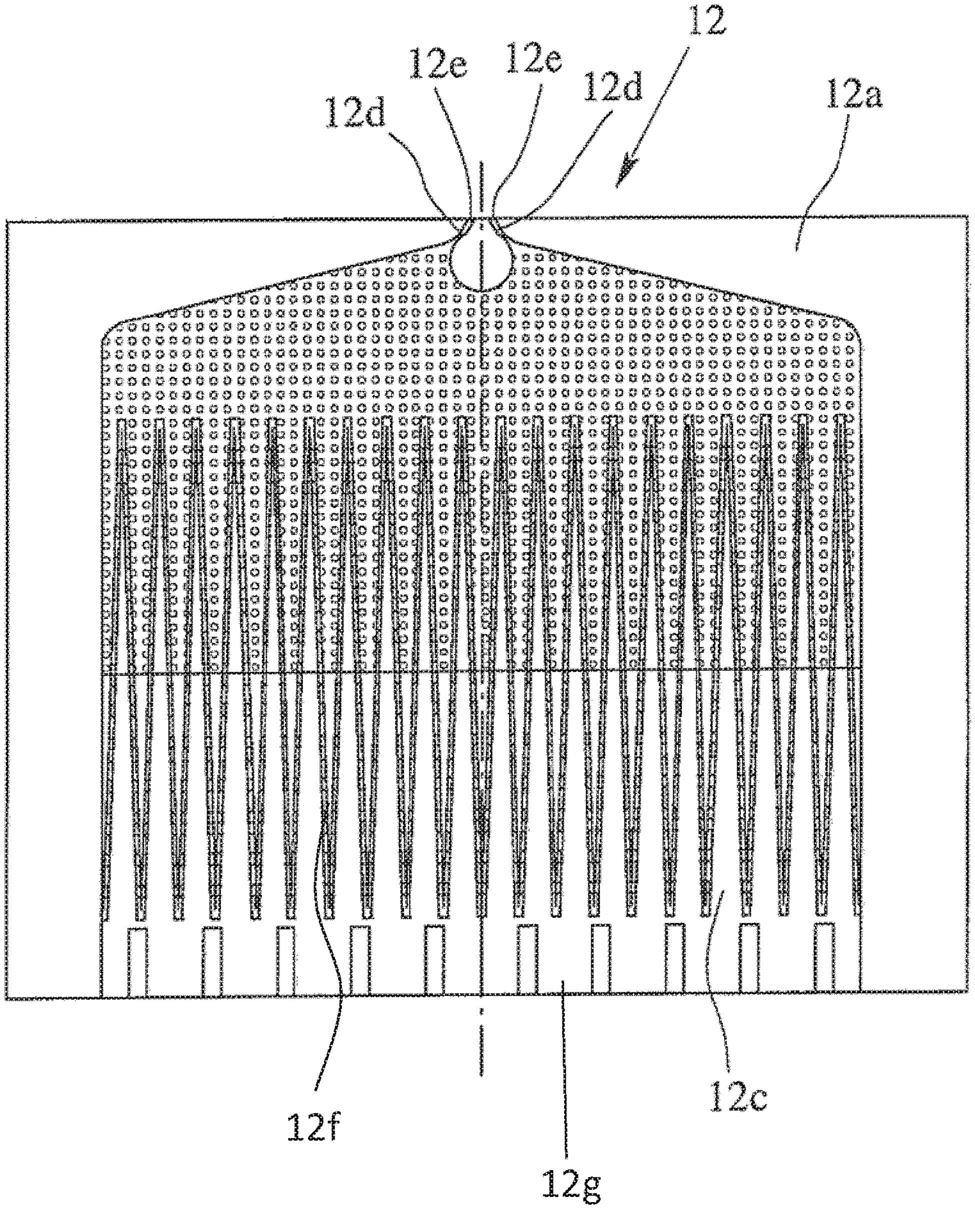
FIG. 3 is a schematic plan view of the microstructure of a nozzle for installation in an atomiser.

To produce inhalable aerosols, most atomiser designs require nozzle structures with very small dimensions. In the case of the embodiment, the dimensions of the nozzle channels (12*d*) of the favoured microstructured nozzle (12) only amount to a few micrometres. The nozzle channels (12*d*) preferably have a rectangular profile with edge lengths of 2 to 10 micrometres (corresponding to the channel height and channel width). In particular, the nozzle (12) has at least one, preferably two outlet openings or nozzle orifices (12*e*) with a rectangular cross-section with edge lengths of 2 to 10 micrometres, particularly preferably 4 to 8 micrometres. The structure of a microstructured nozzle which can be used for insertion is shown in the embodiment in FIG. 3. In the example, the atomisation of the liquid with the atomiser is preferably based on the impaction of two microscopic jets of liquid at high speed: Jets of liquid emerge from the preferably two nozzle channels (12*d*) or the associated nozzle orifices (12*e*) and are directed in such a way that they meet at a defined angle to one another and are nebulised by the forces acting upon impact. If particles accumulate in these nozzle channels (12*d*) during operation of the device, the jets of liquid can optionally be deflected, so that the impaction and thus the atomisation is no longer complete or in the extreme case does not take place at all. For this reason, the particles should already be filtered out as completely as possible from the liquid (2) before the liquid flows into the nozzle channels (12*d*). For the same reason, according to the invention the nozzle is produced from a material which has a non-stick effect based on the components of the medical formulation to be atomised, so that in particular at the liquid/air interface in the outlet region of the nozzle channels (12*d*) no accumulations of material are produced by agglomeration or dehydration.

In the embodiment, the microstructured component forming the nozzle (12) contains not only the actual nozzle channels (12*d*) but also an integrated fine filter (12*f*) which also prevents the smallest particles from entering the nozzle channels. In a favoured embodiment, the nozzle (12) or the microstructured component is composed of a microstructured plate (12*a*) and a flat plate (cover) which covers the structures and is firmly connected to the plate (12*a*). The plate (12*a*) and cover are preferably made of plastics material (not necessarily the same one), wherein the plate (12*a*) or a base plate, from which the plate (12*a*) has been separated out or cut out, has been produced in a moulding process according to the invention. The nozzle (12) preferably has the configuration of a rectangular cuboid, wherein the structures or channels extend in a plane parallel to the two main surfaces of the cuboid. In this case, an inlet opening and/or an outlet opening (nozzle orifice (12*e*)) is in particular arranged on a narrow side of the cuboid (inlet opening or inlet openings and outlet openings or outlet openings are preferably arranged on opposite sides of the cuboid).

The structure enclosed in this way forms along the flow direction at least one, but preferably a plurality of inlet openings with an adjoining common inflow region (12*c*) and, downstream of an inflow region (12*c*), firstly a fine filter (12*f*) designed as a flow filter and then the nozzle channels (12*d*). The filter effect is achieved by a specific arrangement of fixed webs and passages. The zigzag-shaped arrangement of rows of webs with small passages (with significantly smaller cross-sections than the nozzle orifices) with in particular a rectangular profile (the profile is production-related) is particularly preferred. The passage widths in this case amount to only a few micrometres—particles up to a size of approximately 2 micrometres are preferably removed from the liquid before it enters the nozzle channels and later, after atomisation, is inhaled by a user of the inhaler. The microfluidic component preferably has, downstream of the fine filter formed by webs and passages, a common outflow region (upstream of the nozzle outlet), which can optionally also include further structures or filter elements. Further details of possible microstructures for the nozzle (12) or fine filter (12*f*) installed in the nozzle assembly are disclosed in the documents WO94/07607A1, WO99/16530A1, WO05/000476A1, WO07/101557A2 and WO08/138936A2.

The entire system consisting of a pressure generator (5) with drive spring (7), a pre-filter, a fine filter (12*f*) and a nozzle (12) is preferably set up so that during production of the spray mist not only are droplet sizes formed which are adapted to the respirability, but also the spray mist lasts cloud itself so long that the patient can easily adjust his inhalation to it. In this case, spray times of 0.5 to 2 seconds, in particular 1 to 2 seconds, are preferred. The layout of the microstructures, in particular channel diameters and design of the filter system in the atomiser, influences the length the spray time.

FIG. 4 shows schematically a method for producing a microstructure for a moulding tool and a method in which the microstructures of the microfluidic component, in particular of the nozzle (12) or the microstructured plate (12*a*), are then produced with the moulding tool. By comparison with the embodiment of the microfluidic component shown in FIG. 3, the microstructures illustrated in FIG. 4 are shown purely schematically or in a significantly simplified view for better explanation of the production method.

In the method shown here a master component (101) is used, which has substantially the same microstructures as the microfluidic component to be produced in the serial process. In some circumstances, the exact dimensioning of the structures, in particular of channel depths and channel widths, deviates somewhat from the structures to be finally produced, since later moulding steps and, depending upon the materials used, material shrinkages associated therewith must be taken into consideration. The structure heights in the master component (101) are between 2 and 40 μm, in general between approximately 3 and 20 μm, preferably between approximately 4 and 14 μm, in particular between approximately 5 and 8 μm. As shown schematically in FIG. 4*a* (and in FIG. 4*b* in a sectional view according to the partial section S-S in FIG. 4*a*), the master component (101) preferably has not only the microstructures of a microfluidic component to be produced but also of a plurality of preferably identical microfluidic components alongside one another (the production of different microstructures alongside one another is al so possible, but this would be less suitable for serial mass production processes, since then later a separation of various kinds of components in the processes must be taken into consideration). The microstructures (or microstructure groups (102)) corresponding to the individual microfluidic components to be produced are all arranged on the master component (101) in the same orientation. In the case of the master component (101) shown schematically in FIG. 4*a*, for example all the structures corresponding to the inlet openings (12*g*) point in one direction and all the structures (formed by nozzle channels (12*d*)) corresponding to the nozzle outlets are situated opposite them. The microstructure groups (102) (i.e. the microstructures corresponding to the individual microfluidic components to be produced) are arranged in a plurality of parallel rows and columns, so that a later separation can take place, for example with the aid of rectilinear saw cuts between the microstructure groups (102).

The master component (101) is produced from a semiconductor material, such as for example gallium arsenide or silicon, but preferably from a highly doped silicon (in particular in monocrystalline form) (as a result some of the process steps are omitted from the schematic illustrations in FIG. 4*c* to FIG. 4*l*, which were established generally for the use of master components made from any materials). Particularly preferably, a silicon wafer is used, since this exhibits a slight surface roughness and sufficient planarity and parallelism. The preferably plate-shaped material or the silicon wafer is preferably structured in a photolithographic method known in principle from semiconductor technology in conjunction with an ion-assisted reactive dry etching method (an RIE method). A thin layer of silicon is preferably thermally oxidised on the surface of the wafer. The oxide coating serves later for masking the etching of the channel structures. A light-sensitive plastics layer is applied and solidified on this oxide coating in a centrifugal process. Using a mask (preferably made of chrome glass), the plastics layer is exposed step by step in a stepper process, wherein the structures contained two-dimensionally in the mask are reproduced preferably on a reduced scale on the plastics layer (for example in aspect ratios of 5:1 or 10:1). (Alternatively a photo-optical transmission of the structure by means of contact copying via a mask on the scale 1:1 in this plastics layer is also possible, but decreasing imaging ratios facilitate the production of smaller structures and a non-contact guiding of the mask increases the service life of the mask). The plastics layer exposed in such a way is then developed, so that structures are produced in the plastics material according to the exposure. In the next process step, the plastics structures serve as masking for the structuring of the silicon dioxide layer. This structuring preferably takes place by reactive etching with ions, but alternatively the use of wet-chemical etching processes is possible. At the end of the structuring operation, the plastics material is completely removed and U-shaped or rectangular, box-shaped channel structures are located on the silicon wafer, although these channel structures can have almost any surface geometry in plan view.

Optionally, instead of this single-stage structuring process a multi-stage process can also be used in order to produce different structural depths in the master component (101). Thus for example it may be desirable that the passages of the fine filter (12*f*) have a smaller depth than the preceding inflow region (12*c*) and/or the following outflow region. On the one hand, as a result the filter effect of the fine filter (12*f*) is intensified, since now asymmetric particles with longitudinal dimensions greater than the passage width are retained better. It is also possible to achieve an antibacterial filter effect here by analogy with the structures described in WO08/138936A2. On the other hand, the demouldability in later process steps (in particular during the later demoulding of injection moulded microfluidic components from moulding tools produced with the master component (101)) is improved with regard to the comparatively narrow structures.

FIGS. 4*c* to 4*l* show schematically a method by which a microstructure for a moulding tool is produced by means of a master component (101) according to FIG. 4*a* or 4*b*. In the generally more applicable schematic view shown here, the master component can be manufactured from any material, such as for example a plastics material (for example polycarbonate); the schematic view also contains steps which are necessitated by insufficient conductivity of the master component. In the method presented here, the microstructure of the master component (101) is electroformed with a metal, wherein in particular the entire microstructured surface of the master component is covered with electroplated metal. In order then to obtain the moulding tool, the master component (101) must be completely removed; in the region of the microstructures the later moulding tool preferably consists exclusively of the electroplated metal.

FIG. 4*c* shows how the master component (101) is fitted or inlaid or inserted onto a support plate (103). This support plate (103) preferably has a depression (103*a*) suitable for the master component (101), so that the height of the edge (103*b*) of the support plate (103) inserted in the edge region of the master component (101) in the depression (103*a*) is preferably equal to the surface of the inserted master component (101) (i.e. the depth of the depression (103*a*) preferably corresponds to the thickness (101*a*) of the master component (101)). The material and the thickness of the support plate (103) (below the depression (103*a*)) must be selected so that they have a suitable mechanical stability for the later galvanic process. In this process, thermal stresses ensue which, in particular in the case of support plates (103) which are too thin (for example in the case of copper thinner than 8 mm), can lead to deformations due to which the moulding tool thus produced is no longer planar and thus in turn the produced microfluidic structures can be correspondingly poorly capped. Metal plates with a thickness of at least 8 mm are preferably used, since metal can be faced very precisely. For electroplating of nickel or nickel iron, copper is preferably used as material for the support plate (103). When the master component (101) is inserted into the support plate (103), an adhesive is preferably used, so that the master component (101) is fixed in the depression (103*a*) in the support plate (103). In this case or additionally, the lateral (slot-like) intermediate space between the master component (101) and the edge (103*b*) of the support plate (103) is filled with a filling compound (104), for example with epoxy resin. This is so that in the impending metallisation (result shown purely schematically in FIG. 4*d*) the applied, preferably conductive metallisation layer (105) does not tear off at the location of the intermediate space or exhibits no cracks there, but forms a consistent layer (in contrast to the schematic representation in FIG. 4*d*, however, the metallisation layer (105) is thinner by a multiple than the master component (101) and covers heights, depths and walls of the microstructures without forming one single plane).

There is no need to use a support plate (103) and thus to use the process steps explained with the aid of FIG. 4*c* when structured semiconductors such as silicon wafers are used, since they can be further processed directly due to their external form and due to their planar surfaces and in particular their stability. (In the representation of a method based purely on the use of semiconductor master components, the representation of the support plate (103) in FIGS. 4*d* to 4*i* (if applicable) would be omitted).

The metallisation layer (105) preferably consists of chromium and gold, wherein both are applied for example in a sputter process or a vaporisation process. In this case, chromium serves as an adhesive layer between the master component (101) (preferably made of silicon) and the gold. The layer thicknesses here are for example 20-30 nm for chromium and 50-200 nm for gold. In the subsequent electroplating process step, the metallisation layer (105) or the gold layer serves as electrode.

In the preferred case in which a highly doped semiconductor material, in particular highly doped silicon, is used for the master component (101) (and thus the semiconductor exhibits a high conductivity), the metallisations (shown for example in FIG. 4*d*) and for example the costs ensuing due to the sputtering on of gold are omitted. The master component itself would then be directly connected (in particular without any further treatment after production thereof) in a conventional electroplating process as a deposition electrode. Depending upon the use of the part of a moulding tool to be produced or the tool insert to be produced in the entire process, the metal plating with an inert metal such as gold can also have additional advantages, since this layer forms a surface in the later moulding tool and, depending upon the material to be moulded, the moulding on this structured surface can be improved by the inert coating.

FIG. 4*e* shows the master component (101) after the electroplating of a covering metal layer (106) (preferably of nickel or nickel iron or nickel cobalt). (The metallisation layer (105) optionally applied to the master component (101) is not shown in this illustration because of its thinness, but if required it would be located between the master component (101) and the metal layer (106)). In this electroplating, the metal-plated support plate (103) with inlaid master component (101) is placed into an electroplating bath, in particular formed by an electrolyte solution containing nickel (for example a nickel sulfamate electrolyte solution) in a suitable vessel, and the previously applied metallisation layer (105) is connected as electrode or is used as cathode. In the case of the preferred use of a master component made of a highly doped semiconductor material, this master component is preferably placed directly into the electroplating bath or into a suitable casing, in which with the use of an electrolyte solution preferably containing nickel the electroplating process is carried out, and is electrically connected, so that it forms a cathode in the process.

For reasons of mechanical stability, the electroplated layer which is later to form part of the moulding tool or is to form the tool insert for a moulding tool is preferably at least 500 μm, particularly preferably 1 mm thick (for use as film, in the production of a self-supporting tool containing nickel, a layer thickness in the range from 5 mm to 8 mm is preferred). In principle, by means of electroforming, tools with microstructure heights of 2-1000 μm can be produced, and the free intermediate spaces which are present between the microstructures can be approximately 2 μm to a few mm. In particular, using this technique, structures up to aspect ratios of 1:50 can be obtained (based on width to depth of the structure in the μm range). However, in the relevant field of application (production of structures for microfluidic components, in particular nozzles) it is preferable to work only with aspect ratios in the range from 1:4 to 250:1 (depending upon the structure detail).

For the process preferred here (electroplating of a comparatively thin nickel-containing film on a master component, which is comparatively planar per se, with structure depths which are only in the single-digit micrometre range), the electroplated layer on the master component or on the metallisation layer exhibits a suitable planarity of the surface for further processing. However, in some circumstances this is not necessarily the case in particular in the production of thicker (self-supporting) nickel-containing layers, for example with coarser structures, so that in such a case, not favoured here, where appropriate a further process step should be incorporated, in which a planar surface (106*a*) is produced on the electroplated metal, in particular by abrasion of the surface of the electroplated metal. However, during this smoothing of the surface of the metal layer (106) on the side facing away from the master component (101) a specific minimum layer thickness of the metal should remain on the entire surface (result to be seen in FIG. 4*e*) in order to preserve the stability required in the later procedure. (During levelling or abrasion the surface opposite the produced complementary microstructure (106*b*) is processed; the complementary microstructures (106*b*) produced in the metal during electrodeposition are not changed by the abrasion).

FIG. 4*f* shows a preferred process step, such as preferably slot-like markings are applied in particular near the edge of the planar surface (106*a*), wherein the markings serve for further processing of the workpiece (at this time in the example shown the "workpiece" is formed predominantly from the support plate (103), the master component (101) and the metal layer (106), and in the particularly preferred example it is formed for example only by the master component (101) and the metal layer (106)). These markings are preferably slots (106*c*) which later serve for guiding saw blades in a sawing process. As indicated schematically in FIG. 4*f*, the slots (106*c*) are preferably produced in a die-sinking process, wherein an electrode (107) with a protruding contour (107*a*) in a dielectric is led to the planar surface (106*a*) of the metal layer (106). In the die-sinking process, by application of an electrical voltage between the electrode (107) and the metal layer (106) (or between the electrode (107) and the master component (101) when a master component made of a metal or a highly doped semiconductor material is used) an electrical discharge is produced, by which material is removed from the planar surface (106*a*) at the sites predetermined by the protruding contour (107*a*). In the example shown in FIGS. 4*f*, 4*g* and 4*h*, a contour (107*a*) in the form of a rectangular border is used, so that slots (106*c*) which form a peripheral rectangle are produced on the planar surface (106*a*). Saw blades are guided in these slots (106*c*) in a subsequent sawing process. In this case, the sawing lines (108) for this sawing process are indicated in FIGS. 4*g* and 4*h* by way of example. In the example shown, the slots (106*c*) predetermine the position of the cut edges subsequently produced on the workpiece. Preferably only a rectangular blank of the workpiece is provided and the part of the moulding tool or of the tool insert which is produced later has the complementary microstructures (106*b*) to a plurality of microstructure groups (102). However, it is possible (although not expedient with regard to later mass production) to use contours (107), for example in the form of a plurality of rectangles lying alongside one another, and thus already to perform a separation of the microstructure groups (102) in their complementary form during sawing. The ensuing conventional sawing process (for example water jet cutting, rotary sawing etc.) is chosen according to the materials (for example of the support plate and master component) to be severed.

When conventionally obtainable silicon wafers are used for the master components, at this point the process steps (shown schematically in FIGS. 4*f* to 4*g* and FIGS. 4*j* to 4*k*) which serve for the edge machining can optionally be omitted if the deposited metal layer (106) or a film formed thereby (shown schematically in FIG. 4*l*) is already suitable due to its external shape for later use in moulding tools. For example, when typically round, disc-shaped silicon wafers are used for the master components, with correspondingly appropriate geometric design of the electroplating bath circular films of the same diameter can be produced which can be gripped in moulding tools or clamped on the edge. The product which is produced with the resulting moulding tool can then have edge contours which deviate from the circular shape, since for example in the case of an injection mould only a part of the film can constitute a side of the mould to be injected (and the part of the film which is not required does not border on the interior of the moulding tool, but for example forms a clamping region).

The master component (101) is exposed laterally on the workpiece by the edge machining, in particular by the sawing (based on the methods by which machining is performed with a support plate (103)), so that if required it can be easily separated from the support plate (103) (optionally depending upon the adhesive used at the outset in the fixing of the master component (101) in the support plate (103), the support plate (103) can be removed using low traction forces or the adhesive can be loosened under the action of heat or wet chemical action).

Also without a detachment of the support plate (103), the master component (101) is laterally accessible for the wet chemical action because it is exposed at least partially on the edge. The metal layer (106) is preferably separated from the master component (101), in that the master component (101) is preferably wet-chemically dissolved (for example by means of a KOH solution) (see FIG. 4*i*). In this way, a metal plate or metal foil (106*f*) with complementary microstructures (106*b*) is obtained.

If present, the previously deposited adhesive layer is etched out of chromium.

Before installation in a moulding tool, the metal foil (106*f*) is optionally further processed on its edges (see FIGS. 4*j*, 4*k* and 4*l*), in order for example to remove burrs (106*g*) previously produced by successive marking and sawing (shown schematically in FIGS. 4*f* to 4*g*). This is expedient for example when the edge geometry of the metal foil (106*f*) or in particular of a correspondingly structured, self-supporting metal foil which is significant in the configuration of the later moulding tool (i.e. in the case of a foil which is merely to be clamped later, such further processing is not usually necessary). Such edge processing can also be completely omitted for example when a conductive material (metal or highly doped semiconductor) is used for the master component (101). In this case, the electroplated metal layer (106) for the formation of suitable edges or desired edge shapes can be completely severed in a die-sinking process by means of the conductive master component (101) at the locations predetermined by the contour (107*a*) or the material of the master component (101) can be eroded.

In order that, in the case where edge processing is required, the complementary microstructures (106*b*) are protected during this edge processing, they are covered beforehand with a protective coating (109) (for example photoresist) (see FIG. 4*j*). Then the edges of the metal foil (106*f*) are processed in the required manner, for example by removing burrs (106*g*) remaining after the sawing, preferably by abrasion, or the edges overall are abraded (for result see FIG. 4*k*). After this processing, the protective coating (109) is removed again, for example wet chemically (for result see FIG. 4*l*).

For the produced metal plate or metal foil (106*f*) to be used in a moulding tool (110), these are preferably attached magnetically to a retaining plate (112). For the magnetic attachment to the retaining plate (112), the metal plate or metal foil (106*f*) must be ferromagnetic, which is the case after the electroplating preferred here with nickel, nickel cobalt or nickel iron for production of the metal plate or metal foil (106*f*). Preferably, the retaining plate (112) itself is magnetic or contains magnets (111) or constitutes a receptacle for magnets (111). In the embodiment, as shown in FIGS. 4*m* and 4*n* and FIG. 5, the retaining plate (112) (preferably made of metal, for example steel or brass) has at least one depression for receiving at least one magnet (111). A plurality of magnets (111) with separating elements, such as for example separating plates (113), arranged between them are preferably arranged in this at least one depression. Alternatively, the retaining plate (112) has a plurality of depressions for a plurality of magnets (111) which are separated by narrow bars. The dimensions of the magnets (111) and depressions (and, if provided, separating elements or bars) are chosen or co-ordinated with one another in such a way that after insertion of the magnets (111) into the depressions the retaining plate (112) and the magnets (111) form a planar surface onto which the metal plate or metal foil (106*f*) with its planar surface (106*a*) is placed flat and preferably directly.

In this way, the metal foil (106*f*) or the metal plate with the complementary microstructures (106*b*) is retained in the moulding tool (110) by means of magnetic forces (also during the demoulding process).

Preferably an injection moulding process, particularly preferably a plastics injection moulding process, is used as moulding process in the production of the microfluidic components or nozzles. In such an injection moulding process, hollow moulding tools are usually used, which are closed during the introduction of liquefied material or plastics material and are opened after solidification of the material for removal of the produced component or of the basic body having microstructures. The moulding tool (110) schematically shown in FIG. 4*n* is also of this type.

In the example shown (see FIG. 4*n*), the metal foil (106*f*) is preferably also retained in the closed moulding tool (110) by positive engagement or is fixed by clamping of the metal foil (106*f*). With the moulding tool (110) closed, this clamping of the metal plate or the metal foil (106*f*) is preferably produced on the edge between the retaining plate (112) and a further, dish-shaped tool (110*a*).

Due to the fastening of the metal foil (106*f*) or the metal plate with the complementary microstructures (106*b*) only by means of magnetic forces and clamping, after they become worn they can be easily removed from the opened tool and replaced. If thicker (self-supporting) structured metal plates are used, of which the prior production requires comparatively long electroplating process times, these plates can also be fastened by means of positive engagement on suitable contours instead of magnetic retention.

During the moulding process, the tool is exposed to high temperatures and accordingly also to substantial temperature fluctuations. In this connection, the use of metal foil (**106*f*) containing nickel, and in particular metal foils (106*f***) made of nickel cobalt, is preferred because of their stability at the temperatures usually used in moulding processes (in the case of the plastics materials considered here the tool temperatures are typically in ranges up to 190° C.).

Depending upon the melting temperature of the material or plastics material used in the injection moulding process, the moulding tool (110) and thus also the retention means for the metal plate or the metal foil (**106*f*) are exposed to high temperatures. In the injection moulding process, the plastics material, which in some circumstances is liquefied at temperatures of 190 to 350° C., is introduced into the moulding tool (110) or into the hollow mould formed by the moulding tool (110), where it solidifies. This process can optionally also be performed variothermally, which requires control of the tool temperature. After the solidification of the plastics material in the moulding tool (110), this moulding tool or the hollow mould formed by the moulding tool (110) is opened and the basic body having the microstructures is withdrawn. For this purpose, demoulding forces must be applied, which means in particular that a certain application of force is necessary here, in order to release the basic body on its structured side from the shaping tool structures (that is to say the complementary microstructures (106*b*) on the metal foil (106*f*)). Thus the retention of the metal foil (106*f*) in the moulding tool (110) must be robust, such that it withstands the demoulding forces which occur, i.e. retaining forces of the magnets (111) must also be greater than the demoulding forces which occur. In order that the metal foil (106*f*) is also retained in position during demoulding of the injection moulded parts from the still hot moulding tool (110), magnets (111**) made of samarium cobalt (SmCo) are preferably used, of which the magnetic forces are present even at higher temperatures than for example in the case of ferrite magnets or NdFeB magnets (at up to approximately 200° C. the SmCo magnets retain their magnetic force).

Surprisingly, it has been shown that the magnetic retaining force which SmCo magnets exert on a ferromagnetic metal plate or a metal foil (**106*f***) in particular containing nickel can be increased by the use of a plurality of SmCo magnets and can be arranged so that the polarity thereof is alternately oriented.

Thus the magnetic retaining forces which act on the ferromagnetic metal plate or metal foil (**106*f*) are intensified by the use of a plurality of magnet bodies having such an alternating arrangement of the poles. In this case, in particular rectangular, plate-shaped SmCo magnets in a parallel arrangement are used for the magnets (111), wherein the flat sides have the poles and the arrangement is alternating so that in each case two of the same pole types are directed towards one another, wherein they are preferably separated from one another by spacers. One such preferred arrangement can be seen for example in FIG. 5. The plate-shaped magnets (111) are arranged on a retaining plate (112). The retaining plate (112) preferably has a depression which is filled by the magnets (112) and optionally spacers between the magnets (112), wherein the depression is filled up flush with magnets (111) and optionally spacers in such a way that a planar surface is produced on the upper side of the retaining plate (i.e. on the side of the retaining plate (112) which includes the depression). The metal plate with the complementary microstructures or the metal foil (106*f*) is preferably placed directly onto this surface. In this way, the magnets (111) which alternate in the polarisation direction, optionally together with the edges of spacers optionally arranged between the magnets, form a contact surface for the metal plate or metal foil (106*f*). Separating plates (113) which are optionally ferromagnetic are preferably used as spacers. The separating plates (113), like the magnets (111), are preferably rectangular and plate-shaped, wherein the width and length of the plates are identical to those of the magnets (111). Only the thickness of the separating plates (113) differs from the thickness of the plate-shaped magnets (111). The separating plates (113) are preferably thinner than the magnets (111) and have only at most the same plate thickness. Retaining plates (112), magnets (111**) and spacers (if present) are preferably adhered to one another or are inseparably connected to one another in other ways.

As an alternative to the injection moulding shaping process indicated in FIG. **4*n*, the main bodies (which have the microstructures and constitute semi-finished products in the production of the microfluidic components or nozzles) are also produced in different moulding processes, for example in a hot stamping process or in a compression injection moulding process (such as is known for example from the production of CDs or DVDs; a possible process is described for example in EP0537953A2), in which complementary microstructures (106*b***) produced according to the invention are then used. However, compression injection moulding processes are preferably used here only in the production of microfluidic components, when these only have small structural depths, in particular structural depths smaller than 10 μm, preferably smaller than 5 μm. For the production of microfluidic components with greater structural depths, another moulding process (for example plastics injection moulding) should be chosen.

In a hot stamping process, a plastics blank for example is placed in the moulding apparatus, is heated therein (although not necessarily up to liquefaction of the plastics material) and a punch with the complementary microstructures (**106*b***) is pressed onto the heated blank. After cooling of the basic body produced in this way, the punch is moved back and the component is withdrawn.

The basic body produced in a plastics moulding process (injection moulding process, compression injection moulding process or hot stamping process) preferably has at least one but preferably a plurality of microstructure groups (102) which are in the form of grooves on a base plate. With regard to the microfluidic component to be produced or to the nozzle (12), in the application example this base plate or a part of this base plate comprising a microstructure group (102) forms the microstructured plate (**12*a*) which is covered by a cover (12*b*) (see FIG. 4*o*). The cover (12*b*) is preferably plate-shaped or is at least planar on the side facing the base plate or plate (12*a*). Due to the covering, channel structures are produced which are closed along their length, wherein the grooves of the component produced in the plastics moulding process form three walls of a rectangular channel and the fourth wall is formed by the cover (12*b***).

The base plate is preferably covered on its microstructured side by a cover (**12*b*) which jointly covers all microstructure groups (102) on the base plate, wherein the cover (12*b*) and the base plate are preferably inseparably connected to one another. This connection takes place for example by thermocompression bonding, laser bonding, plasma-activated bonding or particularly preferably solvent bonding. Using these connection techniques, it is possible to produce connections between the base plate and the cover which can withstand a liquid internal pressure (for example of up to 1000 bars) such as for example in the atomiser (1**) of the application example. For microfluidic components, in which the liquid is guided at comparatively low pressure, the use of a cover in the form of a foil applied by lamination, sealing or adhesion is also possible.

In addition to the microstructure groups (102), the base plate preferably also has structures which serve as markings in particular in the vicinity of the edge. These may be designations of the type of structure and/or preferably cutting markings, for example. The capped base plate preferably contains a multiplicity of microstructure groups (102), which are first isolated by separation from one another. The separation preferably takes place by sawing. The cutting markings enable the precise application of saw cuts by which the capped base plate is disassembled into the individual microfluidic components (or nozzles). In the case of the production of nozzles (12), in the application example this precision in the sawing is important, since the nozzle orifices (12*e*) and the inlet openings (12*g*) are only exposed upon sawing at the sawing edges.

The described production methods are transferable to the production of many types of microfluidic components for many types of devices in which liquids are conveyed or transported. In particular, the proposed atomiser (1) operates purely mechanically. However, the use of such microfluidic components is not limited to the application in purely mechanical devices for discharging a liquid. It can also be used, for example, in systems in which the discharge of the liquid is driven by propellant gas or by electrical, hydraulic or other pumps. Thus terms such as "pressure generator" are generally understood. In this sense, the present invention can also be used across different sectors; even applications beyond the medical field are possible.

The atomiser shown here serves specifically for dispensing a liquid medical formulation as an inhalable aerosol and is suitable for discharging both aqueous and also for example alcoholic, in particular ethanolic medical formulations.

Preferred constituents of the preferably liquid medical formulation are set out in particular in the documents WO09/047173A2 and WO09/115200A1, which are hereby incorporated in full by reference. In particular, the fluids described in these documents are aqueous or non-aqueous solutions, mixtures, formulations with and without solvent, such as ethanol or the like.

List of references

| | |
|---|---|
| 1 | atomiser |
| 2 | liquid |
| 3 | container |
| 4 | bag |
| 5 | pressure generator |
| 6 | holder (for container) |
| 7 | drive spring |
| 8 | locking ring |
| 9 | hollow piston |
| 10 | non-return valve |
| 11 | pressure chamber |
| 12 | nozzle |
| 12a | plate |
| 12b | cover |
| 12c | inflow region |
| 12d | nozzle channels |
| 12e | nozzle orifices |
| 12f | fine filter |
| 12g | inlet openings |
| 13 | mouthpiece |
| 14 | aerosol |
| 15 | air intake opening |
| 16 | upper housing part |
| 17 | inner housing part |
| 18 | lower housing part |

-continued

List of references

| | |
|---|---|
| 19 | safety closure |
| 20 | spring |
| 21 | container base |
| 22 | piercing element |
| 40 | button |
| 101 | master component |
| 101a | thickness (of the master component) |
| 102 | microstructure group |
| 103 | support plate |
| 103a | depression (in support plate) |
| 103b | edge (of depression in support plate) |
| 104 | filling compound |
| 105 | metallisation layer |
| 106 | metal layer |
| 106a | planar surface (of the metal layer) |
| 106b | complementary microstructure |
| 106c | slot (in metal layer) |
| 106g | burr (on metal foil) |
| 106f | metal foil |
| 107 | electrode |
| 107a | protruding contour (on electrode) |
| 108 | sawing line |
| 109 | protective coating |
| 110 | moulding tool |
| 110a | dish-shaped tool part |
| 111 | magnet |
| 112 | retaining plate |
| 113 | separating plate |

The invention claimed is:

1. A moulding tool (110), comprising:

a metal plate having complementary microstructures (106*b*) or a metal foil (106*f*) with such complementary microstructures (106*b*), where the metal plate or the metal foil (106*f*) is a metal layer (106) produced in an electrodeposition process by means of a microstructured master component (101), and when separated from the master component (101), the complementary microstructures (106*b*) are complementary to microstructures on the master component (101); and a plurality of magnets (111) arranged in parallel and adjacent to one another in such a way that in each pair of adjacent ones of the plurality of magnets (111) alternate or differ with regard to their polarisation direction, wherein the metal plate or the metal foil (106*f*) is made of a ferromagnetic material and is retained at least partially magnetically in the tool by way of the plurality of magnets (111), the complementary microstructures (106*b*) are sized, shaped and positioned such that a micro-structured nozzle for use in a device for administering a liquid medical formulation is produce when the moulding tool (110) operates on plastics injection moulding material, and the micro-structured nozzle resulting from the complementary microstructures (106*b*) are the nozzle sized, shaped and positioned in a way suitable for atomisation of the liquid medical formulation.

2. The moulding tool (110) according to claim 1, wherein:

the microstructured nozzle has a plate (12*a*) with groove-like microstructures which are covered on a long side by a cover (12*b*), and the plate (12*a*) and the cover (12*b*) are made of rigid plastics material and are firmly connected to one another.

3. The moulding tool (110) according to claim 2, wherein the plastics material is a COC, COP, polystyrene, polypropylene, PC, PEEK, PMP or PMMA.

4. The moulding tool (110) according to claim 2, wherein at least one of:

the nozzle has at least one nozzle channel (12*d*), the nozzle is suitable for atomisation of the liquid medical formulation and has at least one nozzle orifice (12*e*), and the nozzle channel has a filter structure.

5. The moulding tool (110) according to claim 2, wherein the nozzle is sized and shaped for dispensing a liquid medical formulation as an inhalable aerosol.

6. The moulding tool (110) according to claim 2, wherein the cover (12*b*) is applied to the plate (12*a*) by thermocompression bonding or laser bonding.

7. The moulding tool (110) according to claim 2, wherein the cover (12*b*) is applied to the plate (12*a*) by plasma-activated bonding or polymer bonding.

8. The moulding tool (110) according to claim 2, wherein the cover (12*b*) is applied to the plate (12*a*) by solvent bonding.

9. The moulding tool (110) according to claim 8, wherein, before the solvent bonding, a solvent is applied to the cover (12*b*) in a spin-coating process.

10. The moulding tool (110) according to claim 2, wherein the basic body covered by the cover (12*b*) is disassembled by cutting or sawing into a plurality of individual nozzles, wherein cuts produced during cutting or sawing are oriented by means of markings on the basic body.

11. The moulding tool (110) according to claim 1, wherein the moulding tool (110) is adapted for use in a plastics moulding process.

12. The moulding tool (110) according to claim 11, wherein the moulding process is one of: a hot stamping process, a compression injection moulding process, and an injection moulding process.

13. The moulding tool (110) according to claim 1, wherein the metal plate or the metal foil (106*f*) is made of at least one of: nickel, a metal containing nickel, nickel iron, nickel cobalt, and contains nickel.

14. The moulding tool (110) according to claim 1, wherein the metal plate or metal foil (106*f*) is retained by at least one of: a plurality of magnets (111), a plurality of uniform magnets (111) and a plurality of magnets (111) made of samarium cobalt.

15. The moulding tool (110) according to claim 1, wherein the microstructured master component (101) is made of at least one of a semiconductor material, and a monocrystalline silicon.

16. The moulding tool (110) according to claim 15, wherein the semiconductor material is highly doped.

17. The moulding tool (110) according to claim 1, wherein the microstructures (106*b*) have a multiplicity of microstructure groups.

18. The moulding tool (110) according to claim 1, wherein the microstructures of the master component (101) are produced in at least one of a photolithographic process, and in conjunction with an ion-assisted reactive dry etching method.

* * * * *